(12) United States Patent
Huertas Muñoz et al.

(10) Patent No.: US 9,943,479 B2
(45) Date of Patent: *Apr. 17, 2018

(54) INJECTABLE LIQUID PARACETAMOL FORMULATION

(75) Inventors: Faustino Huertas Muñoz, Madrid (ES); Raul Fernández Plágaro, Madrid (ES)

(73) Assignee: GENFARMA LABORATORIO S.L., Madrid (ES)

( * ) Notice: Subject to any disclaimer, the term of this patent is extended or adjusted under 35 U.S.C. 154(b) by 1275 days.

This patent is subject to a terminal disclaimer.

(21) Appl. No.: 12/084,541

(22) PCT Filed: Jul. 18, 2006

(86) PCT No.: PCT/ES2006/070108
§ 371 (c)(1),
(2), (4) Date: Mar. 19, 2009

(87) PCT Pub. No.: WO2008/009756
PCT Pub. Date: Jan. 24, 2008

(65) Prior Publication Data
US 2009/0215903 A1     Aug. 27, 2009

(51) Int. Cl.
| A61K 31/167 | (2006.01) |
| A61K 9/08 | (2006.01) |
| A61K 47/26 | (2006.01) |
| A61K 47/12 | (2006.01) |
| A61K 9/00 | (2006.01) |
| A61K 47/20 | (2006.01) |

(52) U.S. Cl.
CPC .......... *A61K 9/0019* (2013.01); *A61K 31/167* (2013.01); *A61K 47/20* (2013.01); *A61K 47/26* (2013.01)

(58) Field of Classification Search
CPC ..... A61K 9/0019; A61K 31/167; A61K 47/26
See application file for complete search history.

(56) References Cited

U.S. PATENT DOCUMENTS

| 4,440,815 A | 4/1984 | Zomorodi et al. |
| 6,028,222 A | 2/2000 | Dietlin et al. |
| 2004/0054012 A1 | 3/2004 | Dietlin |
| 2004/0247627 A1* | 12/2004 | Nguyen-Xuan ............. 424/400 |
| 2006/0084702 A1 | 4/2006 | Nguyen-Xuan |
| 2006/0084703 A1 | 4/2006 | Nguyen-Xuan |

FOREIGN PATENT DOCUMENTS

| AU | 1997 39451 B2 | 2/1998 |
| EP | 0869066 A1 | 10/1998 |
| EP | 0 916 347 | 5/1999 |
| FR | 2 751 875 | 2/1998 |
| FR | 2 809 619 | 12/2001 |
| FR | 2 862 872 | 6/2005 |
| WO | 00/07588 | 2/2000 |
| WO | 02/072080 | 9/2002 |
| WO | 03/033026 | 4/2003 |
| WO | 03/051398 | 6/2003 |
| WO | WO 2004/004705 | 1/2004 |
| WO | 2004/071502 | 8/2004 |
| WO | 2005/053747 | 6/2005 |
| WO | WO 2007/001957 | 1/2007 |

OTHER PUBLICATIONS

Morrison K. "Physical Science Level 3". Pearson Education, 2008. pp. 16-18.*
Remington: The Science and Practice of Pharmacy, 19th Edition. p. 931, p. 1463.
K.T. Koshy, et al. Stability of aqueous solutions of N-actyl-p-aminophenol. J. Pharmaceutical Sciences, Feb. 196, vol. 50 (2), 113-118 (described in specification).
From European Opposition Proceeding: Annex 1—Facts and Arguments, European Patent EP 1889607 B, in the name Genfarma Laboratorio S.L., Opposed by Teva Pharmaceutical Industries, Ltd.
Office Action dated Oct. 26, 2017 corresponding to U.S. Appl. No. 15/076,072.

* cited by examiner

*Primary Examiner* — Leslie A. Royds Draper
(74) *Attorney, Agent, or Firm* — Hogan Lovells US LLP

(57) ABSTRACT

The invention relates to an aqueous paracetamol solution for administration by means of infusion with a pH of between 4.5 and 6, containing at least one substance that can react with fenolates to produce the O-derivatives thereof or other co-ordination compounds. The injectable paracetamol solution has high stability, does not become colored over time and has a minimum impurity content.

4 Claims, No Drawings

INJECTABLE LIQUID PARACETAMOL FORMULATION

FIELD OF THE INVENTION

The present invention relates to an injectable liquid paracetamol composition according to the preamble of claim 1.

BACKGROUND OF THE INVENTION

Paracetamol (n-acetyl-4-aminophenol) is an active ingredient that has been widely used in the last 4 decades in pharmaceutical preparations due to its activity as an analgesic and an antipyretic which was introduced by Von Mering in 1893. It is further well tolerated by human beings and does not alter the acid-base equilibrium, therefore it is widely used to relive pain both in adults and in children and in the elderly. A large number of pharmaceutical preparations to be administered orally or even topically are known. However, it is difficult to obtain a pharmaceutical preparation for injection and particularly, a ready-to-use solution for intravenous perfusion, due to the fact that paracetamol is not very soluble in water and its solutions in aqueous medium are unstable in the presence of oxygen and/or light, being decomposed through a plurality of degradation pathways which are well known and are described for example in the article "Stability of aqueous solutions of N-acetyl-p-aminophenol", by K. T. Koshy and J. L. Lach, J. Pharmaceutical Sciences, Vol 50 (2) (February 1961), p. 113-118. This instability in aqueous medium is shown by the appearance of degradation substances causing a coloring in the solution. The different substances causing the coloring of the solution include benzoquinoimines which are hepatotoxic in humans.

However, the development of color in pharmaceutical solutions and especially in injectable formulations which must be completely transparent involves a serious problem, because the presence of said color is indicative of the existence of unwanted compounds in the formulation and therefore leads to the rejection of the injectable product without being used.

One of the causes of paracetamol degradation is based on chemical oxidation reactions in which the oxygen present in the solution is the main precursor of this degradation. The secondary cause of degradation may be the deacetylation of the amino group generating p-aminophenol which is also quickly degraded producing p-benzoquinoneimine. This deacetylation takes places both at acid pH and (much faster) at basic pH once the phenolate form is present.

In vivo, most of the paracetamol is metabolized through the formation of these phenolate form derivatives, mainly through the gluconated derivative and through the sulfonated derivative:

Obtaining stable paracetamol solutions in aqueous medium can be solved by means of several joint actions.

1) Establishing an optimal pH in which the formation of 4-aminophenol is prevented or minimized, as has been indicated by K. Thomas Koshy and Jon L. Lach in the previous indicated reference "Stability of aqueous solutions of N-acetyl-p-aminophenol", J. of Phar. Sci., Vol 50 No. 2 (1961), 113-118, the hydrolysis of the acetate group of paracetamol is minimized between pH=4.5 and pH 6.0.

2) Preventing the presence of oxygen in solution. This action is described in Spanish patent no. 2,201,316, from the validation in Spain of European patent EP 858,329 B1, issued to Pharmatop SCR. This document discloses a process whereby paracetamol oxidation is prevented by means of eliminating the main element activating the reaction, oxygen, with nitrogen bubbling. By further keeping the solution in a completely hermetic bottle, the stability of paracetamol in solution is ensured for long time periods, with minimal impurity levels and the total absence of color in the solution. It must be deduced by the characteristics of the SCR Pharmatop product that its must be kept in suitable bottles preventing the incorporation of oxygen into the solution and therefore these solutions cannot be stored in individual oxygen-permeable bottles such as plastic materials.

The joint action on the two previous factors allows obtaining a stable paracetamol solution which does not develop color for a long time period.

International patent publication WO2004/071502 A1, issued to Nguyen-Xuan, describes a paracetamol formulation containing a buffer agent with a pKa between 4.5 and 6.5, an isotonic agent and a paracetamol dimer. The stability of paracetamol in solution is attributed to the presence of the paracetamol dimer of formula I produced in situ by treatment of the solution with a temperature between 100° C. and 130° C. for at least 5 minutes. This formulation does not need the elimination of oxygen and can be stored in some plastic materials. However, it has the following drawbacks:

1. Since it does not contain factors preventing the oxidation of paracetamol, polymerization impurities such as the mentioned dimer are generated over time, providing color to the solution and turning it into a product that is unsafe in its use because at the time of its use it is not possible to know if the color is from the formation of paracetamol polymers or benzoquinoneimines or of other substances with an unknown origin.
2. The stability of these solutions is reduced when they are stored in plastic materials such as PVC, the composition of which does not use antioxidants. In other words, they must be stored in plastic materials such as polypropylene, polyolefins, polyethylene, polyethylene

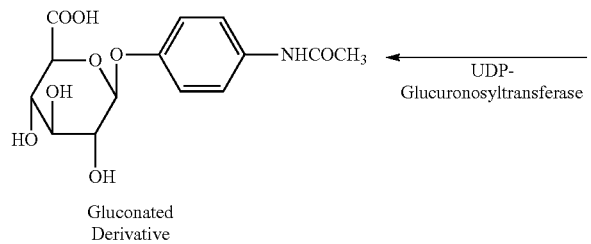

Gluconated Derivative

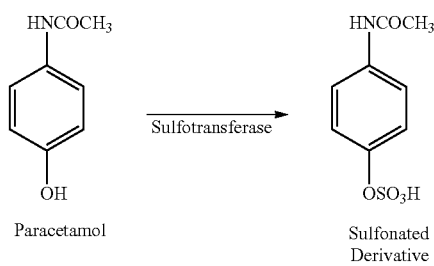

Paracetamol     Sulfonated Derivative vinyl acetate, containing antioxidants and preventing or making the entrance of oxygen into the solution difficult. These materials typically contain one of several of the following antioxidants:

1.—butylhydroxytoluene,
2.—Pentaerythrityl tetrakis(3,5-di-tert-butyl-4-hydroxyphenyl)propionate;
3.—1,3,5-tris(3,5-di-tert-butyl-4-hydroxybenzyl)-s-triazine-2,4,6(1H,3H,5H)-trione;
4.—octadecyl 3-(3,5-di-tert-butyl-4-hydroxyphenyl)propionate;
5.—ethylenebis[3,3-bis[3-(1,1-dimethylethyl)-4-hydroxyphenyl]butanoate];
6.—dioctadecyl disulfide;
7.—2,2',2',6,6',6"-hexa-tert-butyl-4,4',4"-[(2,4,6-trimethyl-1,3,5-benzenetriyl)trismethylene]triphenol;
8.—2,2'-bis(octadecyloxy)-5,5'-spirobi[1,3,2-dioxaphosphinane];
9.—didodecyl 3,3'-thiodipropionate;
10.—dioctadecyl 3,3'-thiodipropionate;
11.—tris(2,4-di-tert-butylphenyl)phosphate;
12.—5 different substances containing the phenyl phosphinite group.
13.—Butylhydroxyanisole Therefore, the problem to be solved by the present invention is to provide an alternative stable injectable paracetamol solution preventing the development of an unwanted color of the solution over time.

The solution to this problem is based on the fact that the authors have identified that when substances that can react with the p-acetyl aminophenolate form, an intermediate chemical species both in the degradation by deacetylation and in oxidation, these paracetamol degradation pathways are significantly reduced, a highly stable injectable paracetamol solution with a minimal content of impurities being obtained. The reason for this is that the formation of intermediate products such as gluconated or sulfonated derivatives with the phenolate form, although they can be unstable in solution, nevertheless significantly reduces paracetamol degradation. Sulfate, gluconate or furfural ions can be found in solution as byproducts generated by this degradation.

Therefore, aqueous paracetamol solutions for their use by perfusion of the invention comprise a substance that can react with phenolates turning them into their O-derivatives or coordination compounds. In a preferred embodiment of the invention, such agents are selected from the group consisting of reducing sugars such as glucose, galactose, fructose; the acid forms of these sugars or their salts, such as gluconate, glucuronate, glucoheptanoate, galactate; chemical species containing sulfur in an oxidation state less than +6, sodium formaldehyde sulfoxylate, sulfites or thiourea or any combination of the previous substances. These compositions produce a solution with very reduced levels of impurities and the absence of color in the solution for long time periods, being able to be stored in antioxidant-free plastic materials.

It is possible to find aqueous paracetamol formulations for perfusion containing antioxidants in the prior art. However, there is no known document studying the different antioxidant power of different substances through the reactivity of phenolate in aqueous solution or its possible practical consequences. The authors have now found that the action on this intermediate product in the paracetamol hydrolysis/oxidation process allows providing different degrees of protection of paracetamol against oxidation in the same pH conditions, such that it is possible to obtain a solution with the aforementioned advantages by suitable selecting the antioxidant or substance that can react with the intermediate phenolate form.

On the other hand, it is known that phenols can generate complexes with metal ions by means of their phenolate form, therefore this fact can also be used to prevent the occurrence of oxidized forms of paracetamol. The formation of metal complexes with phenolate ions can affect the end result for obtaining a stable and colorless paracetamol solution and it is necessary to consider this effect because although generally all of them case a bathochromic effect in the absorption of radiation of paracetamol, shifting the absorption towards more colored area of the spectrum, not all of them do so to the same extent: in the case of cations causing the formation of colored complexes with the phenolate form, as may be the case of iron or zinc, their presence must be prevented by means of adding a suitable chelating agent to the composition, whereas those cations producing colorless forms such as magnesium will favor the stability of the solution since they act as scavengers of the phenolate ions produced.

A very important factor to be considered is that an equilibrium must be achieved between solution color/impurities from paracetamol degradation and impurities from the degradation of the substances used as stabilizers: Although the prior art has described aqueous paracetamol solutions for perfusion comprising glucose as an isotonic agent, it is however necessary to use amounts of the order of 5% m/v to provide isotonicity to the solution, with which amounts a colored solution is obtained after a few months of its production, therefore these solutions would not be suitable in the present invention. It is therefore necessary to use the suitable amount for each stabilizing compound so that said compound shows its stabilizing effect without developing any substantial color over time.

A last factor to be taken into account is that the solubility of paracetamol in aqueous medium is of the order of 12 mg/ml at a temperature of 20° C. and 8 mg/ml at 4° C., such that the process or composition of the solution must prevent the crystallization of paracetamol. This effect is solved by means of filtering the solution through a pore size of 0.45 microns or less, or adding a solubilizing agent as described in international publication WO03033026 issued to BIOREN S. A., disclosing an aqueous paracetamol solution obtained by mixing paracetamol and propylene glycol in citrate medium at a pH comprised between 4.5 and 6.5 and heating said solution at a temperature between 70° C.-130° C.

EXAMPLES

To study the protective effect of different substances which may have an antioxidant activity providing the stability of the paracetamol solution, solutions with a variable composition have been made and stored in glass and PVC (poly(vinyl chloride)) materials to later subject them to wet heat sterilization, which is the safest currently admitted process for injectable solutions.

1) Solutions Stored in Glass Containers

It has been verified that the most stable pH range for paracetamol solutions is between 4.5 and 6.0 and this has been the pH range used for the tests carried out, the buffer agents with a pKa close to this pH range being more favorable because they allow maintaining the optimal pH value in a more constant manner. To that end, it is possible to use buffer agents based con citrates, malates, acetates, lactates, gluconates; and those showing synergistic antioxidant activity such as those containing citric or malic are more favorable.

The following tests have been carried out as tests for evaluating the stability of the solution:
Visual appearance.
Measurement of the absorbance at 320 nm and 500 nm in 10 mm thick quartz cells.
Content of impurities by means of liquid chromatography based on the chromatographic conditions of the European Pharmacopoeia 5th Edition, comparing the relative area with an external paracetamol standard with a known concentration.

After the wet heat sterilization of the solutions obtained, they were subjected to a heat treatment at 100° C. for the glass-bottled solutions and at 70° C. for the solutions stored in plastic material.

The stability of the solution in room temperature conditions of product storage (25° C.) can be predicted by means of observing the characteristics of the solutions subjected to these heat treatments at different times, because, as indicated by K. Thomas Koshy, the degradation kinetics follow the Arrhenius law depending on temperature/time.

The three characteristics studied, visual appearance, absorbance at different wavelengths and content of impurities, are related to one another. The absorbance at 350 nm (yellow) is caused by p-aminophenol, polymerization products, impurities related to the synthesis of paracetamol and benzoquinoneimines; the absorbance at 500 nm (pinkish brown) is caused by benzoquinoneimines and their polymerization. Table 1 indicates the maximum values for the impurity corresponding to the area of the chromatographic peak with the highest value, expressed as % with respect to paracetamol. The sum of all the impurities is indicated as a % total impurity value.

TABLE 1

| | Sodium acetate and/or citrate-NaCl antioxidant; Samples in glass | | | | | | | | | |
|---|---|---|---|---|---|---|---|---|---|---|
| Test | A1 | B1 | C1 | D1 | E1 | F1 | G1 | H1 | I2 | G2 |
| Antioxidant | Sodium ascorbate | Fructose | Thiourea | Sodium dithionite | Curcumin | Sodium nitrite | 0.001% m/V sodium formaldehyde sulfoxylate | Does not contain | 0.5% Glucose | 0.02% m/V sodium formaldehyde sulfoxylate |
| | After wet sterilization in autoclave at 120° C. for 25 minutes | | | | | | | | | |
| Color | Virtually colorless | Colorless | Colorless | Colorless | Colorless | Orangish brown | Colorless | Colorless | Colorless | Colorless |
| Abs 350 nm (AU) | 0.156 | 0.034 | 0.013 | 0.009 | 0.010 | 0.671 | 0.002 | 0.000 | 0.010 | 0.010 |
| Abs 500 nm (AU) | 0.005 | 0.002 | 0.003 | 0.000 | 0.002 | 0.103 | 0.000 | 0.000 | 0.003 | 0.001 |
| Impurities | | | | | | | | | | |
| % impurity, individual maximum value | 0.26 | 0.04 | 0.08 | 0.006 | 0.15 | 5.8 | 0.05 | 0.12 | 0.02 | 0.02 |
| % Total impurities | 0.42 | 0.08 | 0.21 | 0.03 | 0.24 | 8.30 | 0.10 | 0.18 | 0.05 | 0.05 |
| | 16 hours at 100° C. | | | | | | | | | |
| Color | | | | | | | | | | |
| Abs 350 nm (AU) | 0.261 | 0.367 | 0.162 | 0.072 | 0.194 | 1.896 | 0.119 | 0.148 | 0.010 | 0.027 |
| Abs 500 nm (AU) | 0.016 | 0.041 | 0.040 | 0.016 | 0.047 | 0.379 | 0.022 | 0.038 | 0.003 | 0.004 |
| Impurities | | | | | | | | | | |
| % impurity, individual maximum value | — | 0.087 | 0.29 | 0.1 | 0.89 | — | 0.58 | 0.73 | 0.04% | 0.03% |
| % Total impurities | — | 0.29 | 0.60 | 0.22 | 1.26 | — | 0.86 | 1.05 | 0.08 | 0.08 |
| | 24 hours at 100° C. | | | | | | | | | |
| Color | Yellow brown | Brown | Slightly brown | Virtually colorless | Slightly brown | Intense brown | Slightly brown | Brown | Slightly brown | Virtually colorless |
| Abs 350 nm (AU) | 0.420 | 0.566 | 0.249 | 0.096 | 0.291 | — | 0.156 | 0.219 | 0.134 | 0.032 |
| Abs 500 nm (AU) | 0.039 | 0.074 | 0.056 | 0.028 | 0.078 | | 0.040 | 0.060 | 0.044 | 0.005 |
| Impurities | | | | | | | | | | |
| % impurity, individual maximum value | — | 0.09 | 0.32 | 0.20 | 1.0 | — | 0.69 | 0.81 | 0.05 | 0.05 |
| % Total impurities | — | 0.36 | 0.69 | 0.34 | 1.42 | — | 0.97 | 1.13 | 0.11 | 0.11 |

It can be observed that not all the antioxidants stabilize the solution in the same manner. After sterilization, visually, neither the ascorbates nor the nitrites protect paracetamol. The antioxidant-free solution maintains its colorless appearance; however, the antioxidant-free solution is the one containing the highest values of impurities among the colorless solutions. The effect of these substances as antioxidants just as they are is obviously not enough to stabilize the solution.

After 16 hours of treatment at 100° C., it is observed that the solution containing dithionite, glucose or sodium formaldehyde sulfoxylate are the ones with less color, showing values of absorbance at 350 nm that are less than 0.100 absorbance units and at 500 nm less than 0.020 absorbance units.

After 24 hours at 100° C., it can be observed that the formulation containing sodium sulfoxylate at a concentration of 0.02% m/V can equal the stability of the commercial formulation Perfalgan® (obtained according to the process described in the SCR Pharmatop patent), which formulation, kept in its original glass bottle for 24 hours at 100° C., remains colorless with virtually nil absorbances at 350 nm and 500 nm.

2) Solutions Stored in Plastic Material

The same conclusions can be obtained if the evolution of the paracetamol solution in plastic material is observed:

TABLE 2

Sodium acetate and/or citrate - NaCl - antioxidant; Samples in polyvinyl chloride (PVC)

| | Test | | |
|---|---|---|---|
| | T1 | T2 | T3 |
| Antioxidant | Does not contain | 0.5% Glucose | 0.015% m/V sodium formaldehyde sulfoxylate |
| After wet sterilization in autoclave at 120° C. for 25 minutes | | | |
| Color | Colorless | Colorless | Colorless |
| Abs 350 nm (AU) | 0.009 | 0.010 | 0.008 |
| Abs 500 nm (AU) | 0.003 | 0.003 | 0.001 |
| Impurities | | | |
| % impurity, individual maximum value | 0.18 | 0.02 | 0.02 |
| % Total impurities | 0.27 | 0.05 | 0.06 |
| 48 hours at 70° C. | | | |
| Color | Virtually colorless | Virtually colorless | Data not available |
| Abs 350 nm (AU) | 0.063 | 0.046 | |
| Abs 500 nm (AU) | 0.016 | 0.011 | |
| Impurities | | | |
| % impurity, individual maximum value | 0.42 | 0.06 | |
| % Total impurities | 0.58 | 0.09 | |
| 89 hours at 70° C. | | | |
| Color | Brown | Virtually colorless | Colorless |
| Abs 350 nm (AU) | 0.148 | 0.082 | 0.029 |
| Abs 500 nm (AU) | 0.036 | 0.016 | 0.000 |

TABLE 2-continued

Sodium acetate and/or citrate - NaCl - antioxidant; Samples in polyvinyl chloride (PVC)

| | Test | | |
|---|---|---|---|
| | T1 | T2 | T3 |
| Impurities | | | |
| % impurity, individual maximum value | 0.56 | 0.08 | 0.05 |
| % Total impurities | 0.74 | 0.13 | 0.13 |

Both the color and the content of impurities are significantly lower in the paracetamol solutions including a suitable antioxidant. These suitable antioxidants are so not because of their antioxidant activity but because they neutralize paracetamol degradation through the p-acetaminophenolate pathway, which even though its presence is minimal in acid media, its reactivity is significantly higher. The presence of the phenolate form is shown in paracetamol compositions containing sodium ion and at a pH=5.0 by means of liquid chromatography and mass spectrometry, whereby it is possible to obtain chromatographic peaks containing the mass corresponding to the formation of the adduct with sodium through phenolate.

The studied compositions have a much higher stability than that of Perfalgan® when it is stored in plastic material. The Perfalgan® solution in PVC thus has an intense grayish brown color after it is kept for 67 hours at 70° C. with an absorbance of 0.267 AU at 350 nm and of 0.38 AU at 500 nm.

3) Comparison of Solutions Stored in Different Types of Materials

The effect on the color of the same chemical composition according to its storage in different plastic materials (polyolefins and PVC), in which polyvinyl chloride is favored, is observed in the following example.

TABLE 3

Paracetamol solution Color/Absorbance at 350 nm

| | 3.3% citrate-acetate-glucose | | Gluconate-malic |
|---|---|---|---|
| Solution stored in | in Polyolefin | in PVC | in PVC |
| After wet sterilization in autoclave at 120° C. for 25 minutes | | | |
| Color | Colorless | Colorless | Colorless |
| Abs 350 nm (AU) | 0.016 | 0.026 | 0.017 |
| After treatment for 134 hours at 65° C. | | | |
| Color | Virtually colorless | Slight color | Colorless |
| Abs 350 nm (AU) | 0.074 | 0.098 | 0.036 |

The concentration of antioxidant has an important role in the stabilization of the solution because the degradation of such antioxidant in turn generates impurities providing color to the solution. In the case of sugars, they can produce other furfurals and gluconated derivatives, in the case of reducing substances with sulfur, they can produce sulfonated derivatives of paracetamol which can in turn also provide color to the solution, or the inorganic form of sulfates. Depending on the type of stabilizing substance of the solution, its optimal concentration varies: reducing sugars have an optimal effect between 0.5% and 3.0% m/v, sodium formaldehyde sulfoxylate have an optimal effect between 0.001% and 0.02% m/v. It is also observed that the use of the acid form of glucose also prevents the occurrence of color.

As a result, it is possible to obtain a stable paracetamol solution by means of incorporating in the solution antioxidant substances that can react with p-aminophenolates giving rise to their O-derivatives or coordination compounds, preferably selected from the group consisting of reducing sugars such as glucose, galactose, fructose; acid forms of the sugars or their salts such as lactobionate, gluconate; glucuronate; glucoheptanoate, galactate, lactobionate or lactones such as gluconolactone; chemical species containing sulfur in an oxidation state less than +6, sodium formaldehyde sulfoxylate, sulfites or thiourea, and it is possible that these substances can produce derivatives with the phenolate form of paracetamol. Injectable paracetamol solutions with a content of impurities that is less than 0.1% can thus be obtained. The solutions of the invention further have the advantage that they can be contained in glass bottles or bottles of any other type of plastic materials including PVC, and they can be sterilized by heat or filtration.

The invention claimed is:

1. An aqueous perfusion solution which solution has a pH of 5.0, wherein the aqueous perfusion solution consists of paracetamol, glucose, said glucose being in a concentration between 0.5% m/v and 3.0% m/v to stabilize said solution, a chelant and a buffering agent, and wherein the aqueous perfusion solution contains impurities no more than or equal to 0.13% resulting from paracetamol degradation when tested by storing in plastic for at least 89 hours at 70° C.

2. The aqueous perfusion solution according to claim 1, which has been sterilized by heat.

3. The aqueous perfusion solution according to claim 1, wherein the buffering agent is sodium acetate and/or sodium citrate.

4. The solution of claim 1, wherein the aqueous perfusion solution is prepared without the removal of oxygen.

* * * * *

UNITED STATES PATENT AND TRADEMARK OFFICE
CERTIFICATE OF CORRECTION

PATENT NO. : 9,943,479 B2  
APPLICATION NO. : 12/084541  
DATED : April 17, 2018  
INVENTOR(S) : Faustino Huertas Munoz et al.

Page 1 of 1

It is certified that error appears in the above-identified patent and that said Letters Patent is hereby corrected as shown below:

On the Title Page

Item (73), please change the Assignee to read as follows:  
ALTAN PHARMA LIMITED, CO DUBLIN, IRELAND Signed and Sealed this  
Twenty-sixth Day of February, 2019

Andrei Iancu  
*Director of the United States Patent and Trademark Office*